(12) United States Patent
Subramanian

(10) Patent No.: US 6,838,157 B2
(45) Date of Patent: Jan. 4, 2005

(54) METHOD AND APPARATUS FOR INSTRUMENTING A GAS TURBINE COMPONENT HAVING A BARRIER COATING

(75) Inventor: Ramesh Subramanian, Oviedo, FL (US)

(73) Assignee: Siemens Westinghouse Power Corporation, Orlando, FL (US)

( * ) Notice: Subject to any disclaimer, the term of this patent is extended or adjusted under 35 U.S.C. 154(b) by 29 days.

(21) Appl. No.: 10/252,236

(22) Filed: Sep. 23, 2002

(65) Prior Publication Data

US 2004/0202886 A1 Oct. 14, 2004

(51) Int. Cl.[7] .............................. B32B 15/04; C23C 4/00
(52) U.S. Cl. ................... 428/173; 428/320.2; 428/332; 428/596; 428/632; 427/446; 427/455; 427/554; 427/556
(58) Field of Search ................................ 427/446, 455, 427/554, 556; 428/193, 320.2, 332, 632, 633, 596

(56) References Cited

U.S. PATENT DOCUMENTS

| | | | |
|---|---|---|---|
| 3,876,998 A | | 4/1975 | Richter, et al. |
| 3,890,456 A | * | 6/1975 | Dils ........................... 428/216 |
| 4,578,992 A | | 4/1986 | Galasko et al. |
| 4,595,298 A | * | 6/1986 | Frederick .................... 374/144 |
| 4,812,050 A | * | 3/1989 | Epstein et al. ................. 374/1 |
| 4,851,300 A | * | 7/1989 | Przybyszewski ............ 428/623 |
| 4,916,715 A | * | 4/1990 | Adiutori ....................... 374/29 |
| 4,983,034 A | | 1/1991 | Spillman, Jr. |
| 5,144,299 A | | 9/1992 | Smith |
| 5,440,300 A | | 8/1995 | Spillman, Jr. |
| 6,000,977 A | | 12/1999 | Haake |
| 6,142,665 A | | 11/2000 | Haffner et al. |
| 6,197,424 B1 | | 3/2001 | Morrison et al. |
| 6,398,503 B1 | * | 6/2002 | Takahashi et al. ...... 416/241 B |
| 6,437,681 B1 | | 8/2002 | Wang et al. |

OTHER PUBLICATIONS

Sensors for Harsh Enviroments by Direct Write Thermal Spray. By Jon, Longtin, et al. Center for Thermal Spray Research, State University of New York, Stony Brook, NY, and Robert Greenlaw. Integrated Coatings Solutions, Inc., Huntington Beach, Ca.

Laser–Induced Materials And Processes for Rapid Prototyping. By L. Lu, et al. Chapter 6: Metal–Based System Via Laser Melting. The National University of Singapore. Boston, Kluwer Academic Publishers.

Direct–Write Technologies for Rapid Prototyping Applications: Sensors, Electronics, and Integrated Power Sources. Chapter 9: Direct–Write Thermal Spraying of Multilayer Electronics and Sensor Structures, by Sansay Sampath, et al. pp. 261–302. San Diego, CA: Academic Press.

* cited by examiner

Primary Examiner—Jennifer McNeil

(57) ABSTRACT

A method (50) of instrumenting a component (10) having a barrier coating (14). A sensor (76) is embedded within or below the coating. Material forming the sensor is deposited within a trench (80) formed into the barrier coating. The trench is then backfilled with material (70) to protect the sensor from the environment within which the component is operating. In this manner, the sensor may be embedded at any desired location and any desired depth within a barrier coating on a previously fabricated component. An array of sensors (98, 100, 102) may be embedded across the depth of the coating to provide signals indicative of operating conditions across the coating. The signals may be conducted to a connection location (24) by conductors (62, 64) that are deposited within the trench. The trench may be formed with a laser engraving process (54) and the material for the sensor and conductors may be deposited with a selective laser melting process (58).

21 Claims, 3 Drawing Sheets

METHOD AND APPARATUS FOR INSTRUMENTING A GAS TURBINE COMPONENT HAVING A BARRIER COATING

FIELD OF THE INVENTION

The present invention relates to the field of gas turbine engines, and in particular to a method and apparatus for instrumenting a component of a gas turbine engine for monitoring the environment of a coating formed on a surface of the component.

BACKGROUND OF THE INVENTION

Firing temperatures in modern gas turbine engines continue to increase in response to the demand for higher efficiency engines. Super alloy materials have been developed to withstand the corrosive high temperature environment that exists within a gas turbine engine. However, even super alloy materials are not able to withstand extended exposure to the hot combustion gas of a current generation gas turbine engine without some form of cooling and/or thermal insulation.

Thermal barrier coatings are widely used for protecting various hot gas path components of a gas turbine engine. The reliability of such coatings is critical to the overall reliability of the machine. The design limits of such coatings are primarily determined by laboratory data. However, validation of thermal barrier coating behavior when subjected to the stresses and temperatures of the actual gas turbine environment is essential for a better understanding of the coating limitations. Such real world operating environment data is very difficult to obtain, particularly for components that move during the operation of the engine such as the rotating blades of the turbine. Surface mounted sensors must withstand severe mechanical and thermal loads, and if they become dislodged, they may cause damage to downstream portions of the engine. Furthermore, surface mounted sensors provide information only about conditions that exist at the surface of the thermal barrier coating.

Barrier coatings are also used to protect ceramic matrix composite (CMC) components from the high temperature, oxidizing environment within a gas turbine engine. U.S. Pat. No. 6,197,424 describes an abradable coating for insulating a CMC blade tip seal of a gas turbine. The term "barrier coating" as used herein is meant to include coatings applied to a substrate material to provide at least one of thermal insulation, environmental isolation and abrasion resistance.

U.S. Pat. No. 5,440,300 describes a "smart structure" having sensors and actuators embedded within the material of the structure itself. The patent describes the use of embedded sensors for the detection of stress, strain, vibration, cracks, chemical changes and temperature within the structure. However, the patent does not describe how such sensors may be placed within the structure, and the functionality of the sensors is not intended for the high temperature, corrosive environment of a gas turbine engine.

U.S. Pat. No. 6,000,977 describes a composite structure having electrical leads placed between the plies of material during the fabrication of the structure. The leads are terminated in contact pads at a surface of the structure for making contact with mating pads of a mating component. This structure provides improved interconnectivity for the electrical leads when compared to the previous process of simply allowing the leads to extend out of a trough or bore formed in the structure. These structures and processes are particularly well suited for automotive and aviation applications utilizing layered composite materials. However, they are not useful for instrumenting a component of a gas turbine engine that is covered with a layer of a thermal barrier coating material.

SUMMARY OF THE INVENTION

A method for instrumenting a component having a barrier coating is described herein as including: forming a trench to a predetermined depth in a layer of a barrier coating material deposited on a surface of a component; and depositing a material comprising a sensor into the trench. The method may further include depositing a layer of a barrier material into the trench over the sensor. The trench may be formed to a predetermined width to affect a performance parameter of the conductor. The trench may be formed by laser engraving. The method may further include: depositing material into the trench in the form of a powder; and melting the powder in the trench with a beam of laser energy. The trench may be formed to a predetermined depth in the layer of barrier coating material to position the sensor at a desired depth. The method may include: forming a first trench at a first depth in the layer of barrier coating material; depositing material into the first trench to form a first sensor; forming a second trench at a second depth in the layer of barrier coating material; and depositing material into the second trench to form a second sensor.

A method of instrumenting a gas turbine engine including a component having a barrier coating formed thereon is described herein as including: selecting a sensing location on a component of a gas turbine engine; forming a trench in a barrier coating deposited on the component at the sensing location; depositing material into the trench to form a sensor at the sensing location; and backfilling the trench over the sensor with an insulating material. The trench may be formed with a laser engraving process, and the insulating material may be deposited into the trench with a selective laser melting process. The method may further include backfilling the trench with a ceramic thermal barrier coating material using a selective laser sintering process.

A component for use in a gas turbine engine is described herein as including: a substrate; a barrier coating deposited on a surface of the substrate; a trench formed in the barrier coating; a sensor formed in the trench; and a backfill material deposited in the trench over the sensor. The component may further include: the trench extending from a sensing location to a connection location; a conductor connected to the sensor and extending within the trench from the sensing location to the connection location; and the backfill material deposited over the sensor and over the conductor. A bond coat may be deposited between the substrate and the thermal barrier coating, with the trench extending through the barrier coating to a depth proximate an interface between the bond coat and the barrier coating, and the sensor formed proximate the interface between the bond coat and the barrier coating.

A method of instrumenting a component of a gas turbine engine is described herein as including: depositing a sensor onto a surface of a component of a gas turbine engine; and depositing a barrier coating over the sensor.

BRIEF DESCRIPTION OF THE DRAWINGS

These and other advantages of the invention will be more apparent from the following description in view of the drawings that show.

DETAILED DESCRIPTION OF THE INVENTION

Figure 1:
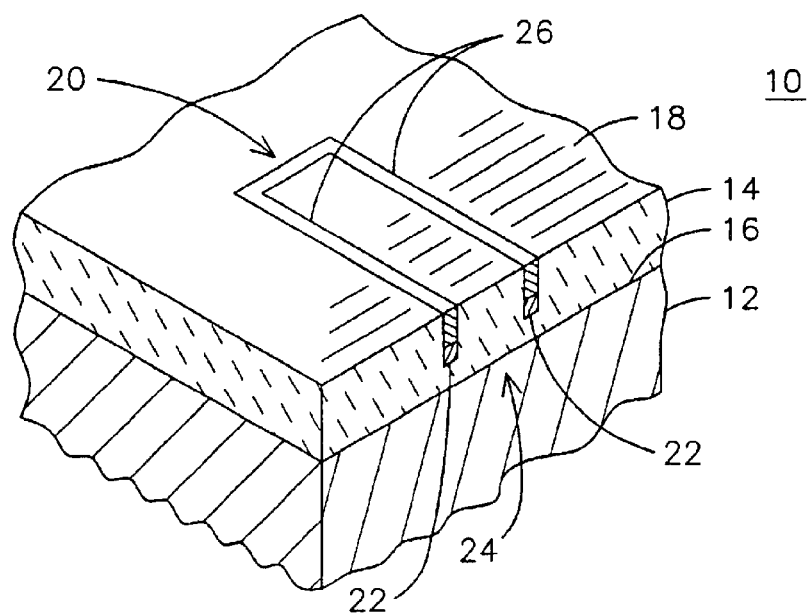
FIG. 1 is a partial perspective view of a component having a sensor embedded within a layer of thermal barrier coating material disposed over a substrate material.

FIG. 1 is a partial perspective illustration of a component 10 formed of a substrate material 12 having a barrier coating such as a layer of thermal barrier coating (TBC) 14 disposed on one surface 16. The component 10 may be part of a gas turbine engine, for example, or any other machine wherein a base material must be protected from an external environment by a layer of a barrier material. In one embodiment, component 10 may be an airfoil member disposed in the hot gas flow path of a gas turbine engine with an oxide or non-oxide ceramic TBC 14 such as mullite, silicon carbide or a zirconium-based ceramic overlying a superalloy substrate material 12. Component 10 may alternatively be fabricated from a ceramic matrix composite (CMC) substrate coated with an environmental barrier coating (EBC). Because the integrity of the thermal barrier coating 14 is critical to the overall integrity of the component 10, it is useful to obtain operating parameter information that directly affects the performance of the coating 14. Such information is obtained by embedding a sensor below the exposed surface 18 of the TBC 14. The sensor is not visible in FIG. 1 but it is located below surface 18 in the sensing location indicated generally by numeral 20. The sensor may be one that provides a signal indicative of temperature, stain, crack initiation, chemical changes, vibration, pressure or other parameter of interest. These sensors themselves could be multi-layered containing a combination of electrodes and the functional body. Conductors 22 also located below surface 18 carry the signal produced by the sensor away from sensing location 20 to a connection location indicated generally by numeral 24 where they can conveniently exit the component 10. The sensor and the conductors 22 are insulated from the surrounding environment by a layer of insulating material 26.

Figure 2:
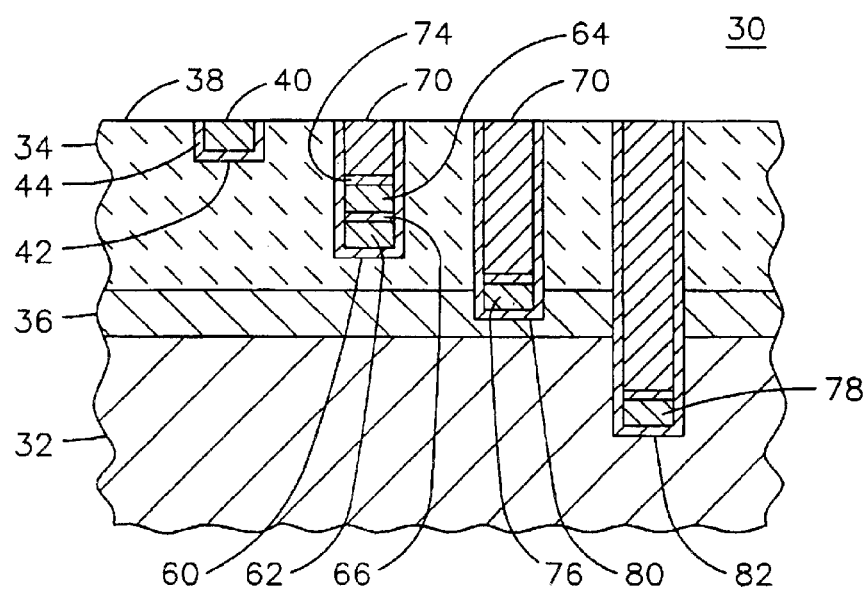
FIG. 2 is a partial cross-sectional view of a component having a plurality of sensors embedded at varying depths below a surface of the component.

FIG. 2 is a partial cross-sectional view of another component 30 having a substrate material 32 covered by a barrier coating such as a layer of a thermal barrier coating material 34 for use in a very high temperature environment. As is well known in the art of TBC coatings, a bond coat 36 such as an MCrAlY material may be deposited on the substrate 32 prior to the application of the TBC material 34 to improve the adherence of the coating 34 to the substrate 32. Component 30 is instrumented by a plurality of sensors embedded at a plurality of depths below a surface 38 of the TBC material 34 that is exposed to the external environment. A first sensor 40 is deposited in a relatively shallow trench 42. Trench 42 may be lined with an electrically insulating coating 44 such as aluminum oxide to prevent the grounding of sensor 40 to the TBC material 34. Sensor 40 may take any form known in the art, for example a thermocouple formed by a bi-metallic thermocouple junction. The surface location of sensor 40 suggests that it may be useful for sensing a parameter related to the external environment, such as temperature or a chemical parameter.

Figure 3:
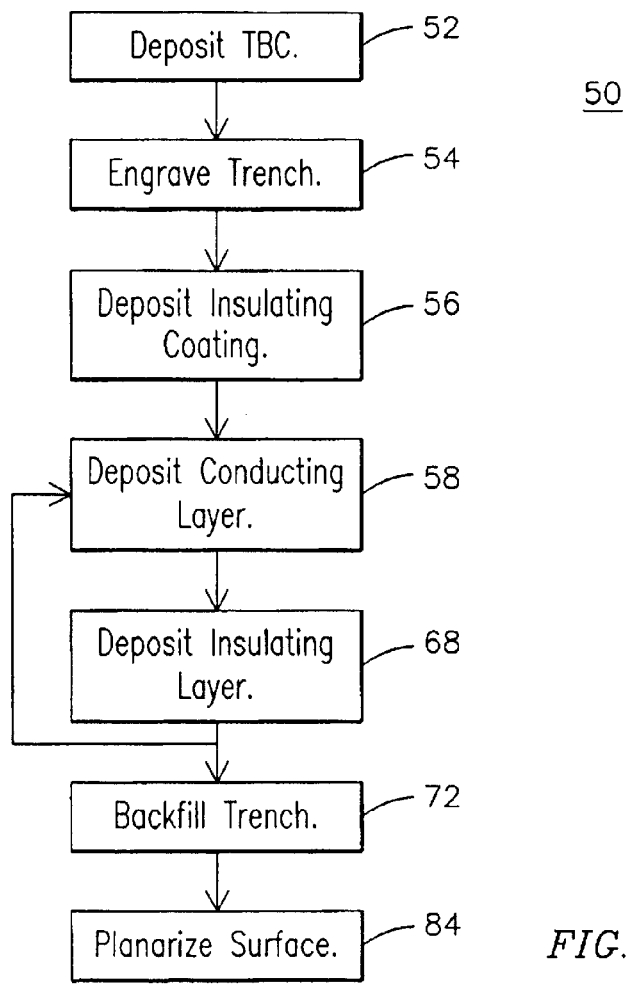
FIG. 3 is a process diagram illustrating steps in a method of manufacturing the component of FIG. 2.

FIG. 3 illustrates the steps of a process 50 that may be used during the manufacturing of the component 30 of FIG. 2. In step 52, a layer of thermal barrier coating material 34 is deposited onto a substrate 32. After step 52, the component is completed in its normal operating shape as it may be used without embedded instrumentation. One skilled in the art may appreciate, therefore, that the process 50 may be applied to newly fabricated components or it may be backfit to an exiting component that is in inventory or that has been in service. In step 54, a trench 42 is formed in a surface 38 of the component 38. Trench 42 may be formed to any desired shape by any known method, such as by laser engraving trench 42 to have a generally rectangular cross-section with a predetermined width and depth. Variables for such a laser engraving process include spot size, power level, energy density, pulse frequency, and scan speed. These variables together affect the trench width, depth, material removal rate and the cost of manufacturing. Trench 42 may have a constant cross-sectional size and shape along its entire length, or it may vary in size and/or shape from one region to another. For example, in the component 10 of FIG. 1, a trench formed in the sensing location 20 may have different dimensions than the trench extending from the sensing location 20 to the connecting location 24, since the sensor and the conductors 22 may have different geometries. The trench 42 may also be inclined to the surface, i.e. varying in depth along its length, which in some applications may provide improved mechanical integrity within the component.

After trench 42 is formed at step 54, an insulating coating 44 may be applied to the surfaces of the trench 42 at step 56 in order to provide electrical isolation between sensor 40 and TBC material 34. Insulating coating 44 may be deposited by any known method such as chemical vapor deposition (CVD) to a thickness sufficient to achieve a desired level of electrical isolation. Once the trench 42 is formed at step 54 and insulated at step 56, the sensor 40 is formed by depositing the appropriate material or materials into trench 42 at step 58. Any known material deposition process providing the desired material properties may be used. Such processes are common in the fields of rapid prototyping, thin and thick film deposition, and thermal spraying, and include, for example, chemical vapor deposition, plasma spray, microplasma spray, cold spray, electroplating, electrophoretic deposition, HVOF, sputtering, CCVD, sol-gel and selective laser melting. Processes typically used for the fabrication of multi-layer thick film capacitors may also be used, such as the application of pastes and tapes of the desired materials. After the deposition of material, a heat input may be used to sinter the material, thereby increasing the mechanical integrity of the sensor. This can be done either by heating using a flame, plasma, furnace annealing or localized laser energy application. In the selective laser melting (SLM) process, powdered material having a predetermined chemistry is deposited into the trench and is then melted with the energy of a laser beam to form the respective portion of the sensor 40 of FIG. 2 or the interconnecting conductors 22 of FIG. 1. For example, to form a thermocouple, platinum powder may be deposited into one portion of trench 42 and solidified by a SLM process. Platinum-rhodium powder is then deposited into a second portion of trench 42, either along the trench length or as a second vertical layer, and solidified by a SLM process to make contact with the platinum material to form the thermocouple junction.

Note that the geometry of trench 42 will have a direct effect on the geometry of the sensor 40. Accordingly, it is possible to affect the operating parameters of sensor 40 or interconnecting conductors 22 by controlling the dimensions of the respective trench 42. For example, the resistance of a conducting line formed within a trench will be affected by the width of the trench. The laser engraving process of step 54 may be closely controlled to achieve a desired trench geometry. Commercially available processes for depositing a conductor onto a flat surface by thermal spraying do not produce the fine features that may be necessary for sensors and conductive lines. Such processes rely on a subsequent material ablation process to achieve a desired geometry. Because trench 42 provides control of the width of the feature, no such trimming step is needed in the process 50 of FIG. 3.

FIG. 2 also illustrates a second trench 60 formed in the TBC material 34 to a second depth that is farther below surface 38 than trench 42. By forming a plurality of trenches 42, 60 at a plurality of depths below surface 38, it is possible to place sensors at more than one depth within the component 30, thereby further augmenting the available operating parameter data. In the embodiment of FIG. 2, trench 60 contains two vertically stacked conducting layers 62, 64 separated by an insulating layer 66. The conducting layers 62, 64 may form two portions of a sensor, or two conducting lines for connecting a sensor to a connecting location. As illustrated in FIG. 3, the two conducting layers 62, 64 may be formed by first depositing conducting layer 62 at step 58, and then depositing an insulating layer 66 at step 68 using any desired deposition technique, such as CVD. Steps 58, 68 are then repeated to deposit conducting layer 64 and insulating layer 74. The width of these layers is controlled by the width of trench 60 and the thickness of these layers may be controlled as they are deposited to achieve predetermined performance characteristics. For example, the thickness of insulating material 66 will affect the impedance between the two conducting layers 62, 64. Conducting layer 64 is then isolated from the external environment by backfilling the trench 60 with a barrier material such as thermally insulating material 70 at step 72. Insulating material 70 may be the same material as TBC material 34 or a different material having desired characteristics. Insulating material 70 may be deposited by any known deposition technique, including CVD, thermal spraying, selective laser melting, or selective laser sintering. Selective laser melting and selective laser sintering processes are known in the art, as exemplified by Chapters 6 and 7 of "Laser-Induced Materials and Processes For Rapid Prototyping" by L. Lu, J. Y. H. Fuh, and Y. S. Wong, published by Kluwer Academic Publishers and incorporated by reference herein.

Additional sensors 76, 78 may be disposed at preselected depths within component 30 by forming respective trenches 80, 82 to appropriate depths. Trenches 80, 82 are backfilled with insulating material 70 to the level of surface 38 at step 72. Planarization of surface 38 may be performed at step 84, if necessary, such as when surface 38 forms part of an airfoil. By forming a trench to a desired depth, a sensor may be embedded to within the TBC material layer 34, to within the bond coat material layer 36, to within the substrate material 32, or to a depth of an interface between any two of these layers. Thus it is possible to develop actual operating parameter data across a depth of a component or across the depth of the thermal barrier coating. Such data may be useful for confirming design assumptions and for updating computerized models, and it may also be useful as an indicator of damage or degradation of a TBC coating. For example, a sensor 78 embedded below the TBC material 34 may produce a signal indicating a significant temperature rise in the event of cracking or spalling of the layer of TBC material 34. Alternatively, the detection of a predetermined level of vanadium, sodium or sulfur deposits by an embedded sensor 76 may announce conditions that would give rise to spalling and failure of the TBC coating 34 if the component were to remain in service for an extended period. This process facilitates the placement of sensors at any location on a fully assembled and coated part. Electrochemical sensors on the component surface can play an important role in determining the nature and effect of corrosion products present in the surrounding environment.

Figure 4:
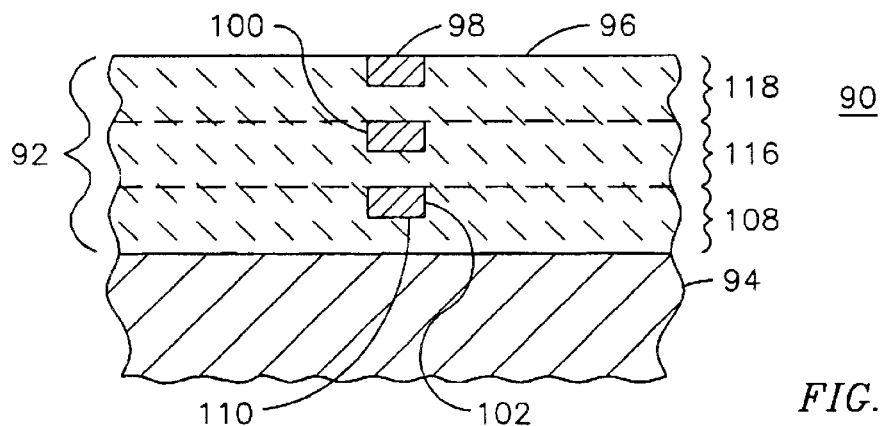
FIG. 4 is a partial cross-sectional view of a component having a plurality of sensors embedded at varying depths below a surface of the component.

FIG. 4 illustrates a component 90 having a barrier coating 92 disposed over a substrate 94. Embedded within the coating 92 at three different depths below surface 96 are sensors 98, 100, 102. Although the Figures illustrate sensors as singular blocks, one may appreciate that the sensors may be multi-layer devices with a plurality of electrodes and a sensing body disposed there between. The structure of FIG. 4 may be produced by a process 104 that can best be understood by referring to both FIGS. 4 and 5. At step 106 a first layer 108 of thermal barrier coating 92 is deposited by any known method. A first trench 110 is then engraved in the first layer 108 at step 112. A sensor 102 is then deposited within trench 110 at step 114. An electrical insulator (not shown) may optionally be deposited within the trench 110 and over the sensor 102 if necessary depending upon the electrical properties of the thermal barrier coating layer 92. Subsequently, a second layer 116 of TBC 92 is deposited over the first layer 108 and over sensor 102, as indicated by the arrow returning to step 106 in FIG. 5. The steps of engraving a trench 112 and depositing a sensor 114 are then repeated to form sensor 100. The steps of FIG. 5 may be repeated again to form sensor 98, with the respective sensors 98, 100, 102 being stacked above each other along a line that is perpendicular to the surface 96 or spaced horizontally apart from each other, in any combination thereof, to provide signals representative of a parameter across the thickness of the TBC 92. The layers 108, 116, 118 of the thermal barrier coating 92 may be formed of identical material or may have some property that varies among them, and sensors 100, 102 may be used to measure a parameter that exists proximate the intersection of the respective layers 108, 116, 118.

Figure 5:
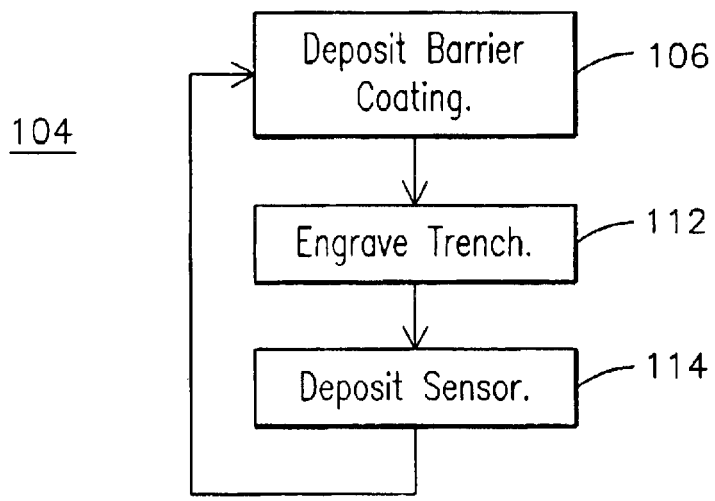
FIG. 5 is a process diagram illustrating steps in a method of manufacturing the component of FIG. 4.
Figure 6:
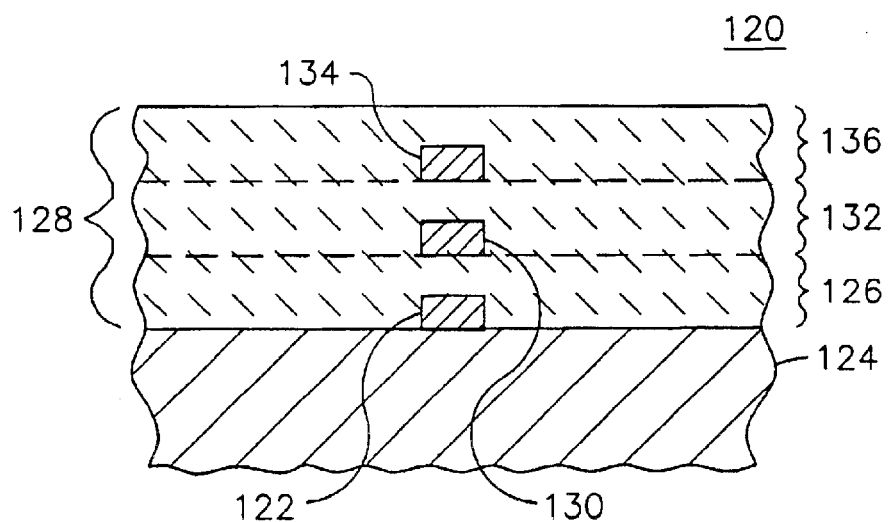
FIG. 6 is a partial cross-sectional view of a component having a plurality of sensors embedded at varying depths below a surface of the component.

FIG. 6 illustrates a component 120 that may be formed using the process of FIG. 5 but without the step 112 of engraving a trench. A first sensor 122 is deposited onto a surface of a substrate 124. Subsequently, a first layer 126 of a barrier coating 128 is deposited over the sensor 122. A second sensor 130 is then deposited over the first layer 126. A second layer 132 of barrier coating 128 is then deposited, followed by the deposition of a third sensor 134 and third layer 136 of barrier coating. In this manner, one or more sensors 122, 130, 134 may be embedded at a plurality of depths within the confines of a wall of a component 120. One may appreciate that the same component 120 may be formed without the first sensor 122 by depositing the sensor 130 onto a surface of the component after it has received a first layer 126 of barrier coating material. Such a structure may be useful for monitoring the amount of wear of an abradable coating, since each of the sensors 134, 130, 122 may become exposed at a different time as the coating 128 undergoes wear due to abrasion. Signals generated by the respective sensors 134, 130, 122 are responsive to the wear of coating 128 and may be used in an improved clearance control program for predicting the remaining useful life of an abradable coating and/or for estimating the amount of leakage past an abradable seal.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

I claim:

1. A method for instrumenting a component having a barrier coating, the method comprising:

forming a trench to a predetermined depth in a layer of a barrier coating material deposited on a surface of a component;

depositing a material comprising a sensor into the trench, and depositing a layer of a barrier material into the trench over the sensor.

2. The method of claim 1, further comprising:

depositing a first material into a first portion of the trench; and depositing a second material into a second portion of the trench, the second material making electrical contact with the first material.

3. The method of claim 1, further comprising:

forming the trench to extend from a sensing location to a connection location on the component; and depositing at least one layer of material into the trench at the sensing location to form a sensor; and depositing a layer of a conducing material into the trench to form a conductor from the sensing location to the connection location for conducting a signal generated by the sensor to the connection location.

4. The method of claim 3, further comprising forming the trench to a predetermined width to affect a performance parameter of the conductor.

5. The method of claim 1, further comprising:

depositing a first layer of conducting material into the trench;

depositing a layer of an insulating material into the trench to form an insulator over the first layer of conducting material; and depositing a second layer of conducting material into the trench over the insulator.

6. The method of claim 1, further comprising forming the trench to a predetermined width to affect a performance parameter of the sensor.

7. The method of claim 1, further comprising forming the trench by laser engraving.

8. A method for instrumenting a component having a barrier coating, the method comprising:

forming a trench to a predetermined depth in a layer of a barrier coating material deposited on a surface of a component;

depositing a material comprising a sensor into the trench;

forming the trench to extend from a sensing location to a connection location on the component; and depositing at least one layer of material into the trench at the sensing location to form a sensor;

depositing a layer of a conducting material into the trench to form a conductor from the sensing location to the connection location for conducting a signal generated by the sensor to the connection location; and refilling the trench with a layer of a barrier material.

9. A method for instrumenting a component having a barrier coating, the method comprising:

forming a trench to a predetermined depth in a layer of a barrier coating material deposited on a surface of a component;

depositing a material comprising a sensor into the trench;

depositing material into the trench in the form of a powder; and melting the powder in the trench with a beam of laser energy.

10. A method for instrumenting a component having a barrier coating, the method comprising:

forming a trench to a predetermined depth in a layer of a barrier coating material deposited on a surface of a component;

depositing a material comprising a sensor into the trench forming the trench to a predetermined depth in the layer of barrier coating material to position the sensor at a desired depth;

forming a first trench at a first depth in the layer of barrier coating material;

depositing material into the first trench to form a first sensor;

forming a second trench at a second depth in the layer of barrier coating material; and depositing material into the second trench to form a second sensor.

11. A method for instrumenting a component having a barrier coating, the method comprising:

forming a trench to a predetermined depth in a layer of a barrier coating material deposited on a surface of a component;

depositing a material comprising a sensor into the trench;

depositing a first layer of thermal barrier coating material onto a surface of the component;

forming a first trench in the first layer of thermal barrier coating material;

depositing material into the first trench to form a first sensor;

depositing a second layer of thermal barrier coating material onto the first layer of barrier coating material;

forming a second trench in the second layer of thermal barrier coating material; and depositing material into the second trench to form a second sensor.

12. The method of claim 11, wherein the second trench is disposed above the first trench along a line perpendicular to the surface.

13. A method of instrumenting a gas turbine engine, the gas turbine engine including a component having a barrier coating formed thereon, the method comprising:

selecting a sensing location on a component of a gas turbine engine;

forming a trench in a barrier coating deposited on the component at the sensing location;

depositing material into the trench to form a sensor at the sensing location; and backfilling the trench over the sensor with an insulating material.

14. The method of claim 13, further comprising forming the trench with a laser engraving process.

15. A method of instrumenting a gas turbine engine, the gas turbine engine including a component having a barrier coating formed thereon, the method comprising:

selecting a sensing location on a component of a gas turbine engine;

forming a trench in a barrier coating deposited on the component at the sensing location;

depositing material into the trench to form a sensor at the sensing location;

backfilling the trench over the sensor with an insulating material; and depositing the insulating material into the trench with a selective laser melting process.

16. A method of instrumenting a gas turbine engine, the gas turbine engine including a component having a barrier coating formed thereon, the method comprising:

selecting a sensing location on a component of a gas turbine engine;

forming a trench in a barrier coating deposited on the component at the sensing location;

depositing material into the trench to form a sensor at the sensing location;

backfilling the trench over the sensor with an insulating material; and backfilling the trench with a ceramic thermal barrier coating material using a selective laser sintering process.

17. A component for use in a gas turbine engine comprising:

a substrate;

a barrier coating deposited on a surface of the substrate;

a trench formed in the barrier coating;

a sensor formed in the trench; and a backfill material deposited in the trench over the sensor.

18. The component of claim 17, further comprising:

the trench extending from a sensing location to a connection location;

a conductor connected to the sensor and extending within the trench from the sensing location to the connection location; and the backfill material deposited over the sensor and over the conductor.

19. The component of claim 17, further comprising:

a plurality of trenches formed in the thermal barrier coating at respective different depths below a surface of the thermal barrier coating;

a sensor formed in each trench; and a backfill material deposited in each trench over the respective sensor.

20. A component for use in a gas turbine engine comprising:

a substrate;

a barrier coating deposited on a surface of the substrate;

a trench formed in the barrier coating;

a sensor formed in the trench;

a backfill material deposited in the trench over the sensor; and a bond coat deposited between the substrate and the thermal barrier coating the trench extending through the barrier coating to a depth proximate an interface between the bond coat and the barrier coating; and the sensor formed proximate the interface between the bond coat and the barrier coating.

21. A method of instrumenting a component of a gas turbine engine, the method comprising:

depositing a sensor onto a surface of a component of a gas turbine engine;

depositing a barrier coating over the sensor;

depositing a second sensor over the barrier coating; and depositing a second barrier coating over the second sensor.

* * * * *